US007902152B2

(12) United States Patent
Reid et al.

(10) Patent No.: US 7,902,152 B2
(45) Date of Patent: Mar. 8, 2011

(54) USE OF COBRATOXIN AS AN ANALGESIC

(75) Inventors: Paul F. Reid, Plantation, FL (US); Zheng Hong Qin, Plantation, FL (US)

(73) Assignee: Receptopharm, Inc., Plantation, FL (US)

(*) Notice: Subject to any disclaimer, the term of this patent is extended or adjusted under 35 U.S.C. 154(b) by 664 days.

(21) Appl. No.: 11/642,312

(22) Filed: Dec. 19, 2006

(65) Prior Publication Data

US 2007/0190167 A1 Aug. 16, 2007

Related U.S. Application Data

(60) Provisional application No. 60/751,663, filed on Dec. 20, 2005.

(51) Int. Cl.
*A61K 38/16* (2006.01)

(52) U.S. Cl. ......................... 514/12.1; 424/520; 424/542

(58) Field of Classification Search ........................ None
See application file for complete search history.

(56) References Cited

U.S. PATENT DOCUMENTS

| | | | | |
|---|---|---|---|---|
| 3,888,977 | A * | 6/1975 | Sanders | 424/542 |
| 4,341,762 | A * | 7/1982 | Haast | 424/184.1 |
| 2004/0192594 | A1 * | 9/2004 | Reid et al. | 514/12 |
| 2005/0031608 | A1 * | 2/2005 | Reid et al. | 424/94.65 |

OTHER PUBLICATIONS

The term "Substantially"—Merrian-Webster Online Dictionary, at the web at—http://www.merriam-webster.com/dictionary, pp. 1-2, accessed online on Jun. 13, 2009.* van Esveld L.W. Preparation of "Cobra toxin" for clinical purposes, especially for the treatment of cancer pains, Biochemische Zeitschrift 1936, 283: 343-357, entire German document.* van Esveld L.W. Preparation of "Cobra toxin" for clinical purposes, especially for the treatment of cancer pains, Biochemische Zeitschrift 1936, 283: 343-357, English translation of the entire document is provided, see pp. 1-23.*

Pu X.C. et al. A novel analgesic toxin (Hannalgesin) from the venom of King Cobra (Ophiophagus hannah), Toxicon, 1995, 33(11): 1425-1431, entire document.*

U2: Grace Ng, Deadly venom's saving grace: It may protect lives as local firm ails to process King Cobra toxin into a potent painkiller and blood-clot inhibitor, The Straits Times, Friday, Apr. 15, 2005, section H16/Home (One page).*

V2: Wang S. et al. Preparation of venom and its analgesic activity, Zhongcaoyao, 1986, 17(1): 7-9, Entire document (in Chinese).*

W2: Wang S. et al. Preparation of venom and its analgesic activity, Zhongcaoyao, 1986, 17(1): 7-9, English Abstract only.*

WebMD- Rheumatoid Arthritis Guide, Online Publication -Article Link: http://www.webmd.com/rheumatoid-arthritis/guide/coping-with-pain, accessed on May 6, 2010 (pp. 1-3).*

WebMD- Multiple Sclerosis Guide, Online Publication -Article Link: http://www.webmd.com/multiple-sclerosis/guide/treating-multiple-sclerosis-pain, accessed on May 6, 2010 (pp. 1-2).*

Berkeley Daily Gazzette, Jan. 4, 1941, p. 3, section "Snake Venom", (Only Pertinent Section Has Been Attached) downloaded on May 6, 2010 from http://news.google.com/newspapers?id=a84oAAAAIBAJ&sjid=eAYGAAAAIBAJ&pg=1100,357641&dq=shingles+cobra+toxin&hl=en.*

Antil-Delbeke et al. Molecular Determinants by Which a Long Chain Toxin from Snake Venom Interacts with the Neuronal a7-Nicotinic Acetylcholine Receptor, The Journal of Biological Chemistry, Sep. 22, 2000, vol. 275, No. 38, pp. 29594-29601.*

U2: Rajendra W. et al. "Toxins in anti-nociception and anti-inflammation"—A review, Toxicon, 2004, vol. 44, pp. 1-17.*

Macht, David I. Experimental and Clinical Study of Cobra Venom As An Analgesic. Proc. Natl. Acad. Sci. 22:61-71, 1936.

Damaj, M. I et al. Antinociceptive Responses To Nicotinic Acetylcholine Receptor Ligands . . . J. Pharmacol. and Exp. Therapeutics 284(3):1058-1065, 1998.

Chen, Z-X et al., A long-form alpha-neurotoxin from cobra venom produces potent opoid-independent analgesia. Acta Pharmacolog. Sinica 27: 402-8, Apr. 2006.

Zhang H-L et al., A short-chain alpha-neurotoxin from Naja naja atra produces potent cholinergic-dependent analgesia. Neuroscience Bulletin 22(2): 103-109, Mar. 2006.

Zhang et al., Analgesic effects of receptin, a chemically modified cobratoxin from Thailand cobra venom. Neuroscience Bulletin 22(5): 267-273, Sep. 30, 2006.

* cited by examiner

*Primary Examiner* — Jon P Weber
*Assistant Examiner* — Satyendra K Singh
(74) *Attorney, Agent, or Firm* — McLaren Legal Services; Margaret J. McLaren, Esq.

(57) ABSTRACT

A composition of matter for an analgesia and its method of use is disclosed. The method of use is for the treatment of chronic pain, especially to the treatment of heretofore intractable pain as associated with advanced cancer. The pain associated with neurological conditions, rheumatoid arthritis, viral infections and lesions is also contemplated. The method includes administering to a host an alpha-neurotoxin that is characterized by its ability to blocking of the action of acetylcholine at nicotinic acetylcholine receptors.

16 Claims, No Drawings

USE OF COBRATOXIN AS AN ANALGESIC

CROSS REFERENCE TO OTHER APPLICATIONS

This application is with and claims the filing date as to common subject matter with Provisional Patent Application Ser. No. 60/751,663 filed Dec. 20, 2005.

BACKGROUND OF THE INVENTION

1. Field of the Invention

The present invention relates to a protein composition of matter and a method for the treatment of chronic pain, especially to the treatment of heretofore intractable pain as associated with advanced cancer. The pain associated with neurological conditions, rheumatoid arthritis, viral infections and lesions may also respond to treatment with the present invention. The composition consists of an alpha-neurotoxin in acceptable carrier base for either parenteral, oral or topical administration.

2. Description of the Prior Art

Research into the pharmacological properties of natural products led to the identification of many compounds with a potent biological activity, which can result in clinically useful therapeutic agents (Verdine, 1996). Plant, microbial and animal toxins are of particular interest, due to their strong pharmacological activity and their selectivity for the site of action. They can be employed directly as therapeutic agents or can serve as starting points for drug design (Harvey et al., 1998).

Bee venom has been employed for centuries to relieve rheumatism and recent studies have shown the product to have useful analgesic properties that support the clinical observations. Snake venom also found extensive use as a therapeutic including pain relief (Williams, 1960). In Van Esveld's 1936 publication "Preparation of Cobratoxin for clinical purposes, especially for the treatment of cancer pains" and by reference to other publications of the same era namely Macht (1936, PNAS 22, pg 61-71) the term cobratoxin was employed in lieu of cobra venom. Cobratoxin, as a distinct neurotoxin, would not be isolated for several decades. Macht's description for the preparation of venom for clinical administration is quite similar to that of Van Esveld, where he describes the preparation of several venoms for use in the treatment of cancer-associated pain: Naja haje, Naja naja and Naja tripudian. Naja tripudian, the venom source for Van Esveld, was often a misidentified species and most often associated with Asian spitting snakes. Spitting snakes are a very poor source of cobratoxin regardless of their geographic location, more likely the neurotoxic component was cobrotoxin, and often tend to be more cytotoxic than neurotoxic. The use of venoms have fallen out of favor with the scientific community.

U.S. Pat. No. 5,364,842 describes the use of omega-conopeptides having defined binding/inhibitory properties in the treatment of chronic pain. In that patent is described omega-conopeptides having related inhibitory and binding activities that enhance the effects of opioid compounds in producing analgesia in mammalian subjects. In addition, these compounds may also produce analgesia in the absence of opioid treatment. Another requisite property of anti-nociceptive omega-conotoxin compounds, in accordance with the invention, is their ability to specifically inhibit depolarization-evoked and calcium-dependent neuro-transmitter release from neurons. In the case of anti-nociceptive omega-conopeptides, inhibition of electrically stimulated release of acetylcholine at the myenteric plexus of the guinea pig ileum is predictive of anti-nociceptive activity. U.S. Pat. No. 6,399,574 similarly describes the use of conantokin peptides which are antagonists of the NMDA receptor. However, these peptides must be delivered intrathecally in order to be effective.

There are several neurotoxins with different biological functions and mechanisms of action in snake venoms. Crotamine from the South American rattlesnake (*Crotalus durissus terrificus*), a myonecrotic toxin, was reported to produce analgesia in mouse models of pain that suggested having a potency up to 30 times greater than morphine (Mancin et al., 1998). Postsynaptic neurotoxins are commonly found in the venoms of *Hydrophiidae* and *Elapidae*, and can be divided into two types: short-chain alpha-neurotoxin (60-62 residues and four disulfides bonds)[1] and long-chain alpha-neurotoxin (66-74 residues and five disulfides bonds)[3]. Both short- and long-chain postsynaptic alpha-neurotoxins have a similar biological property; namely, binding to acetylcholine receptors (AchR). In animal models, Cobrotoxin, a short-chain neurotoxin with high affinity for muscle type AchRs, produced strong analgesic effects through an opiate-independent mechanism (Chen and Robinson, 1990). Cobrotoxin is sold in China as a component of an analgesic formulation.

Other references of interest include two patents, Haast, U.S. Pat. No. 4,341,762; Cosford, et al., U.S. Pat. No. 5,585,388, which claims compounds as modulators of acetylcholine receptors. Literature references of interest are: Chuang L. Y., Lin S. R., Chang S. F. and Chang C. C. Toxicon 27:211-219 (1989); Dierks R. E., Murphy F. A., and Harrison A. K. Am. J. Pathol. 54: 251-274 (1969); Tsiang H., de la Porte S., Ambroise D. J., Derer M. And Koenig J.; J. Neuropathol. Exp. Neurol. 45: 28-42; Tu A. T.; Ann. Rev. Biochem. 42:235-258 (1973); Carstens E, Anderson K A, Simons C T, Carstens M I, Jinks S L. Psychopharmacology (Berl) 2001 August; 157(1): 40-5 "Analgesia induced by chronic nicotine infusion in rats: differences by gender and pain test."; Chen, R., Robinson, S E. Life Sci 1990; 47:1949-1954. "Effect of cholinergic manipulations on the analgesic response to cobrotoxin in mice."; Damaj, M. I., Fei-Yin, M., Dukat, M., Glassco, W., Glennon, R. A. and Martin, B. R., JPET 1998 284:1058-1065, "Antinociceptive Responses to Nicotinic Acetylcholine Receptor Ligands after Systemic and Intrathecal Administration in Mice."; Damaj M I, Meyer E M, Martin B R. Neuropharmacology 2000 October; 39(13):2785-91 "The antinociceptive effects of alpha7 nicotinic agonists in an acute pain model."; Decker M W, Meyer M D, Sullivan J P. Expert Opin Investig Drugs 2001 October; 10(10):1819-30 "The therapeutic potential of nicotinic acetylcholine receptor agonists for pain control."; Irnaten M, Wang J, Venkatesan P, Evans C, K Chang K S, Andresen M C, Mendelowitz D. Anesthesiology 2002 March; 96(3):667-74 "Ketamine inhibits presynaptic and postsynaptic nicotinic excitation of identified cardiac parasympathetic neurons in nucleus ambiguus."; Kwon, Y. B., Kim, J. H., Yoon, J. H., Lee, J. D., Han, H. J., Mar, W. C., Beitz, A. J., Lee, J. H. Am J Chin Med 2001; 29(2):187-99 "The analgesic efficacy of bee venom acupuncture for knee osteoarthritis: a comparative study with needle acupuncture.", Lieb K, Treffurth Y, Berger M, Fiebich B L. Neuropsychobiology 2002; 45 Suppl 1:2-6 "Substance P and affective disorders: new treatment opportunities by neurokinin 1 receptor antagonists?"; Mancin, A., Soares, A., Andriao-Escarso, S., Faca, V., Greene, L., Zuccolotto, S., Pela, I., Giglio, J. Toxicon. 36(12):1927-1937 (1998) "The Analgesic Activity of Crotamine, A Neurotoxin From *Crotalus durissus terrificus* (South Anerican Rattlesnake) Venom: A Biochemical and Pharmacological Study"; Miller, K. D., Miller, G. G., Sanders, M. and Fellowes, O., "Inhibition of virus-induced plaque formation by atoxic derivatives of purified cobra neurotoxins", (1977) Biochim. Biophys. Acta., 496, 192-196; Min, C. K., Owens, J., Weiland, G. A. Mol Pharmacol 1994 February; 45(2):221-7 "Characterization of the binding of [3H]substance P to the nicotinic acetylcholine receptor of Torpedo electroplaque."; Schaible H G, Ebersberger A, Von Banchet G S. Ann N Y Acad Sci 2002 June; 966:343-354 "Mechanisms of Pain in Arthritis."; Schmidt B L, Tambeli C H, Gear R W, Levine J D. Neuroscience 2001; 106(1):129-36 "Nicotine withdrawal hyperalgesia and opioid-mediated analgesia depend on nicotine receptors in nucleus accumbens."; Shiraishi M, Minami K, Uezono Y, Yanagihara N, Shigematsu A, Shibuya I. Br J Pharmacol 2002 May; 136(2):207-16 "Inhibitory effects of tramadol on nicotinic acetylcholine receptors in adrenal chromaffin cells and in *Xenopus* oocytes expressing alpha7 receptors."; Williams, E. Y., J Natl Med Assoc. 1960 September; 52:327-8. "Treatment of trigeminal neuralgia with cobra venom."

SUMMARY OF THE INVENTION

It is an object of the invention to provide a composition of matter and method of its use for treating pain associated with advanced cancer, neuropathy, painful viral infections and their lesions in addition to rheumatic pain.

It is a further object of the invention to provide a composition and therapy for the treatment of pain of the aforementioned type, whose composition and therapy are safe, effective and may be administered over long periods of time.

Other objects will be apparent to those skilled in the art from the following disclosures and claims appended hereto.

The present invention accomplishes the above-stated objectives, as well as others, as may be determined by a fair reading and interpretation of the entire specification. The cobratoxin is prepared by fractionation of the whole venom, neurotoxic fractions or from recombinant sources.

DETAILED DESCRIPTION OF THE INVENTION

As required, detailed embodiments of the present invention are disclosed herein; however, it is to be understood that the disclosed embodiments are merely exemplary of the invention which may be embodied in various forms. Therefore, specific functional details disclosed herein are not to be interpreted as limiting, but merely as a basis for the claims to be later appended and as a representative basis for teaching one skilled in the art to variously employ the present invention in virtually any appropriate circumstance.

Chronic or intractable pain, such as may occur in conditions such as degenerative bone diseases and cancer, is a debilitating condition which is treated with a variety of analgesic agents, and often opioid compounds, such as morphine.

In general, brain pathways governing the perception of pain are still incompletely understood. Sensory afferent synaptic connections to the spinal cord, termed "nociceptive pathways" have been documented in some detail. In the first leg of such pathways, C- and A-fibers which project from peripheral sites to the spinal cord carry nociceptive signals. Polysynaptic junctions in the dorsal horn of the spinal cord are involved in the relay and modulation of sensations of pain to various regions of the brain, including the periaqueductal grey region (McGeer). Analgesia, or the reduction of pain perception, can be effected directly by decreasing transmission along such nociceptive pathways. Analgesic opiates are thought to act by mimicking the effects of endorphin or enkephalin peptide-containing neurons, which synapse presynaptically at the C- or A-fiber terminal and which, when they fire, inhibit release of glutamate and substance P. The key transmitter is glutamate that activates N-methyl-d-aspartate (NMDA) and non-NMDA receptors on spinal cord neurons. Substance P (SP) is a neuropeptide which is abundant in the periphery and the central nervous system, where it is colocalized with other neurotransmitters such as serotonin or dopamine. SP has been proposed to play a role in the regulation of pain including migraine and fibromyalgia, asthma, inflammatory bowel disease, emesis, psoriasis as well as in central nervous system disorders.

The synthesis of analgesics, particularly of morphine-like compounds, has always been a point of major interest in drug research. For decades, scientists throughout the world have attempted to develop effective analgesics by "re-building" the morphine molecule, considering its constitution a combination of certain "basic skeletons" from which they started their syntheses. Meperidine hydrochloride (also known as Dolantin or Demerol) is one such synthetic narcotic analgesic. It is one-tenth as potent an analgesic as morphine and its analgesic effect is halved again when given orally rather than parenterally. The onset of activity occurs within 10-45 minutes with a duration of 2-4 hours. It has superceded morphine as the preferred analgesic for moderate to severe pain. It has been found to be particularly useful for minor surgery, as in orthopedics, ophthalmology, rhinology, laryngology, and dentistry. It is also used in parenteral form for preoperative medication, adjunct to anesthesia and obstetrical analgesia. Like morphine, its binding to opioid receptors produces both psychologic and physical dependence with overdosing causing severe respiratory depression in addition to a number of other undesirable side effects and drug interactions.

Although calcium blocking agents, including a number of L-type calcium channel antagonists, have been tested as adjunct therapy to morphine analgesia, positive results are attributed to direct effects on calcium availability, since calcium itself is known to attenuate the analgesic effects of certain opioid compounds (Ben-Sreti). EGTA, a calcium chelating agent, is effective in increasing the analgesic effects of opioids. Moreover, in some cases, results from tests of calcium antagonists as adjunct therapy to opioids have been contradictory; some L-type calcium channel antagonists have been shown to increase the effects of opioids, while others of these compounds have been shown to decrease opiold effects (Contreras).

Due to the limitations of such analgesics, a number of novel alternatives are currently under investigation, including neuronal nicotinic acetylcholine receptor (nAChR) agonists. Acute administration of nicotine induces analgesia with subsequent development of tolerance. Interestingly, in nicotine-naive rats, injection of the nicotinic receptor antagonist mecamylamine into the nucleus accumbens (where the site for activity of substances of abuse such as opioids has been implicated in pain modulation) blocked antinociception produced by either systemic morphine, intra-accumbens co-administration of a mu- and a delta-opioid receptor agonist, or noxious stimulation (i.e., subdermal capsaicin in the hindpaw). Intra-accumbens mecamylamine by itself precipitated significant hyperalgesia in nicotine-tolerant rats which could be suppressed by noxious stimulation as well as by morphine. Maneckjee et al found that in-vitro that lung cancer cell growth could be suppressed by opioids and this activity was antagonized by nicotine. Thus, nicotinic receptors have been found to play a role in modulating pain transmission in the CNS. Activation of other cholinergic pathways by nicotine and nicotinic agonists has been shown to elicit antinociceptive effects in a variety of species and pain tests. During the 1990s, the discovery of the antinociceptive properties of the potent nAChR agonist epibatidine in rodents sparked interest in the analgesic potential of this class of compounds (Decker et al., 2001). The identification of considerable nAChR diversity suggested that the toxicities and therapeutic actions of the compound might be mediated by distinct receptor subtypes and, accordingly, epibatidine and its derivatives identified nicotinic acetylcholine receptors with mainly alpha4 receptors though receptors with alpha3 were also sensitive to these compounds. The involvement of alpha7 nicotinic receptors in nicotinic analgesia has been assessed through spinal (i.t.) and intraventricular (i.c.v.) administration in mice. Dose-dependent antinociceptive effects were seen with the alpha7 agonist choline after spinal and supraspinal injection using the tail-flick test (Damaj et al., 2000). Furthermore, alpha7 antagonists MLA and alpha-bungarotoxin significantly blocked the effects of choline. These studies suggested that activation of alpha7 receptors in the CNS elicits antinociceptive effects in an acute thermal pain model.

However, in contradiction of the above, nicotinic antagonists may also have a role in pain relief. Tramadol and Ketamine have been used clinically as analgesics however, until recently, their mechanism of analgesic effect was unknown. Studies showed that Tramadol inhibited nicotinic currents carried by alpha7 receptors expressed in *Xenopus* oocytes (Shiraishi et al.). It also inhibited both alpha-bungarotoxin-sensitive and -insensitive nicotinic currents in bovine adrenal chromaffin cells. It was concluded that tramadol inhibited catecholamine secretion partly by inhibiting nicotinic AChR functions. The alpha7 subtype was one of those inhibited by tramadol. Ketamine was found to inhibit the nicotine-evoked presynaptic facilitation of glutamate release (Irnaten et al.). Alpha-bungarotoxin, an antagonist of alpha7 containing nicotinic presynaptic receptors, blocked specific Ketamine actions. It was concluded that Ketamine inhibits the presynaptic nicotinic receptors responsible for facilitating neurotransmitter release, as well as the direct ligand-gated inward current. Alpha-cobratoxin, a protein with a molecular weight of 7831 and 71 amino acids, and its homologue, alpha-bungarotoxin (BTX), preferentially target the alpha7 and alpha1 nicotinic acetylcholine receptors (NAchR) in nerve and muscle tissue, respectively, and functions by preventing activation of such acetylcholine receptors in pre- and post-synaptic membranes.

The analgesic effect of snake venom proteins has been known since antiquity and several authors have pointed out the efficiency of the administration of crude cobra or rattlesnake venoms in the treatment of trigeminal neuralgias, tabetic and pain caused by tumors. Obviously, at the time crude venoms were employed without even an adequate knowledge of the source or mechanism. Sometimes venoms from cobras captured in India or South Africa were employed indistinctly (See Haast, U.S. Pat. No. 4,341,762). A number of neurotoxins from venoms have demonstrated antinociceptive properties such as epibatidine, conotoxin SX111, crotamine and cobrotoxin. The use of crotoxin solely to relieve pain was recently proven. Since the filing of the related Provisional Patent Application described at the beginning of this Application, the inventors of this invention have participated with others in publishing a study showing the efficacy of CTX in treatment of pain. The article was entitled "A long-form α-neurotoxin from cobra venom produces potent opioid-independent analgesia," and the date was Apr. 27, 2006. It appeared in Acta Pharmacologica Sinica by Blackwell Publishing, pages 402-408.

Cobratoxin targets the NAchR in nerve and muscle tissue and functions by preventing depolarization of post-synaptic membranes through regulation of sodium ion channels. The toxicity of these molecules is founded upon their relative affinity for the receptor which far exceeds that of acetylcholine. Binding to the specific target is mediated primarily through electrostatic interactions of amide groups on the toxin to carboxyl groups on the receptor. High salt concentrations can interfere with such interactions. Alpha-bungarotoxin (and its' homologue, cobratoxin) has found great utility as a molecular probe in the study of neuro-muscular transmission and ion channel function. So far 8 different types of nicotinic AchR alpha subunits have been identified with variable pharmacological profiles. It has been found that a homologue, kappa-bungarotoxin, has a higher affinity for the neuronal species of acetylcholine receptors. Cobratoxin and alpha-bungarotoxin have the highest affinity for nicotinic AchRs containing the alpha 1, 7, 8 & 9 subunits (for a review see Lucas, 1995, Coloqoun and Patrick, 1997). Also it has been found that some nicotinic AchRs can conduct calcium ions which has direct effects upon neurotransmission and secretion.

Therefore, the proposed dual mechanism of cobratoxin suggests that the anti-nociceptive effect could result from the impairment of acetylcholine activation of pre- and postsynaptic NAchRs. The blockade of NachRs on the postsysnaptic surface would simply short circuit the pain signal whereas the effects on the presynaptic receptors could mediate the release of other neurotransmitters similarly to the analgesics Tramadol and Ketamine described above.

The production of CTX from venom sources is published and relatively straight forward (see Miller et al., 1977). The neurotoxin has also been cloned and expressed in a bacterial host (Antil S, Servent D and Menez A. J Biol Chem (1999) December 3; 274(49):34851-8) though it is abundant and easily obtained from natural sources in order to study the effect of mutations on its interactions with the acetylcholine receptor. Cobratoxin was tested two pain models; hot-plate and acetic writhing tests with both mice and rats as described in the Apr. 27, 2006 article. The neurotoxin was administered intraperitoneally (ip) and effects were measurable 2 hours post administration and reached a maximum at 3 hours. Intracerebroventricular (icv) administration revealed subtle differences in the analgesia provided by this route of administration. It appeared to be effective in the acetic acid writhing assay though without effect in the hot plate test.

Atropine, a muscarinic acetylcholine receptor agonist could block the effects of cobratoxin in the acetic acid writhing test only when employed at high doses. It had no effect on the efficacy of cobratoxin in the hotplate test. The mechanism by which this inhibition occurs is not readily discernible. Naloxone, an opiate blocker, did not antagonize the activity of cobratoxin suggesting that the analgesic effects did not involve opiate receptors.

To rule out the possibility that CTX's effects on pain response was caused by impairment of motor activity, mice pretreated with the highest dose of CTX (68 μg/kg, ip) were evaluated for spontaneous mobility 1, 2, 3 h after drug administration with an Animex apparatus. The spontaneous mobility of mouse did not change with treatment at the highest dose of CTX (68 mg/kg) used in the study as compared with saline-treated mice.

CTX appears to have efficacy when administered ip and icv though with subtle differences. The demonstration of analgesic activity following ip administration is important for practical application suggestion that the drug would be active when administered subcutaneously or intravenously. This represents an improvement over other analgesic peptides such as conotoxins (SNX111). For topical applications, the applicable concentration of the present neurotoxin range from a minimum of 1 microgram per gram of base up to 1 mg per gram. The applicable topical concentrations of venom are 5-6 fold greater than that for the purified neurotoxin as the neurotoxin accounts for approximately 10% of the composition of the venom. The average drug concentration of 2-10 microgram per gram of base is preferable. The rate of application can range from an infrequent, as needed basis, to several applications per day particularly where the application is for the control of pain. The treatment of a condition like shingles may require 4 to 5 topical applications per day in order to reduce pain.

Example 1

Effects of CTX on Pain Responses in Mice and Rats

Analgesia is conveniently measured in one or more of a number of animal models, in which an animal's response to a given pain stimulus is measured. One such model is the hotplate test. Briefly, in this test, a animal is positioned on a hot plate and is exposed to a standard heat source, and the time that the animal voluntarily endures the heat, prior to licking its' paws, is recorded. Analgesics, particularly opioid analgesics, prolong this time.

The animals used were 10 per group, female mice (Kunming Strain), with a weight of 18-25 g, provided by Center of Animal Research, Suzhou University, China. CTX at 30, 45, or 68 μg/kg (ip) exhibited a dose-dependent prolongation in the latency for the mouse to response to a pain stimulation induced by heat. The analgesic effect of CTX appeared at 2 h and peaked at 3 h after drug administration. The $ED_{50}$ of the antinociceptive effect of CTX was 57.6 μg/kg (35.32-93.93, 95% confidence limit) in the hotplate test.

CTX elicited a dose-dependent inhibition of the writhing response to acetic acid administration. The $ED_{50}$ of the antinociceptive effect of CTX was 54.04 μg/kg (41.04-71.16, 95% confidence limit) with acetic acid-writhing test. The efficacy of CTX in analgesia was comparable to that of Cobrotoxin.

Example 2

Analgesic Actions of Centrally Administered CTX

In mice, intra-cerebral ventricular (icv) administration of CTX (4.5 μg/kg), 1⁄12 of the systemic dose of CTX, significantly reduced the writhing response induced by acetic acid ($p<0.05$), indicating that icv injection of CTX had marked analgesic effects. In the rat hotplate test, administration of CTX (4.5 μg/kg) to periaqueductal gray (PAG), 1⁄12 of systemic dose of CTX, did not produce a significant analgesic action.

Example 3

Human Subject with RA

A male, aged 76 with diagnosed RA which produced pain in his hands utilized alpha cobratoxin in a cream base at a concentration of 2 μg cobratoxin per gram of cream base. Application was on an as needed basis. The patient observed a decrease in pain characterized as allowing him to feel more comfortable. Along with the loss of pain was an increase in mobility in the areas to which the therapeutic was applied. The therapeutic produced a positive effective within 20 minutes and relief lasted several hours.

What is claimed is:

1. A method of inhibiting or controlling pain in a host, comprising administering to the host, a pharmaceutical composition of matter consisting of a therapeutically effective amount of a long-chain alpha-neurotoxin protein isolated from the venom of a snake of the *Naja* genus, and formulated in a pharmaceutically acceptable carrier base, wherein the isolated long-chain alpha-neurotoxin protein comprises between 66 to 74 amino acid residues, and wherein the administration is effective in inhibiting or controlling pain.

2. The method of claim 1 wherein the composition of matter is formulated for parenteral administration, including administration by intravenous, intramuscular or subcutaneous routes.

3. The method of claim 1 wherein the composition of matter is formulated for topical administration.

4. The method of claim 1, wherein the host is a human subject experiencing pain.

5. The method of claim 4, wherein the composition is administered at intervals ranging from once per week to several times a day.

6. The method of claim 1, wherein the isolated long-chain alpha-neurotoxin protein is an alpha-cobratoxin protein, comprising 71 amino acid residues.

7. The method of claim 1, wherein the composition of matter is formulated for oral administration.

8. The method of claim 2, wherein the therapeutically effective composition for parenteral administration is formulated at a neurotoxin dosage of between 0.004 mg/kg and 0.07 mg/kg of body weight.

9. The method of claim 3, wherein the therapeutically effective topical composition comprises between 1 microgram and 1 mg of the long-chain alpha-neurotoxin protein per gram of base.

10. The method of claim 3, wherein the topical formulation in a cream base is effective in providing rapid and lasting pain relief within about 20 minutes of application.

11. The method of claim 1, wherein the pain is thermal pain associated with exposure of the body of the host to excessive heat.

12. The method of claim 1, wherein the pain is associated with exposure of the body of the host to an acid.

13. The method of claim 1, wherein the pain in the host is pain from shingles.

14. The method of claim 1, wherein the isolated long-chain alpha-neurotoxin protein is prepared from a fraction of whole venom or from a neurotoxic fraction isolated from whole venom.

15. The method of claim 1, wherein the host is an animal subject experiencing pain.

16. The method of claim 4, wherein the composition is administered on an as needed basis.

* * * * *